(12) United States Patent
Piccini et al.

(10) Patent No.: US 11,460,529 B2
(45) Date of Patent: Oct. 4, 2022

(54) METHOD AND SYSTEM FOR IMPROVING MAGNETIC RESONANCE IMAGES

(71) Applicants: SIEMENS HEALTHCARE GMBH, Erlangen (DE); CENTRE HOSPITALIER UNIVERSITAIRE VAUDOIS, Lausanne (CH)

(72) Inventors: Davide Piccini, Prilly (CH); John Heerfordt, St. Sulpice VD (CH); Christopher Roy, Lausanne (CH); Matthias Stuber, Romanel-sur-Lausanne (CH)

(73) Assignees: Siemens Healthcare GmbH, Zurich (CH); Centre Hospitalier Universitaire Vaudois, Lausanne (CH)

(*) Notice: Subject to any disclaimer, the term of this patent is extended or adjusted under 35 U.S.C. 154(b) by 96 days.

(21) Appl. No.: 16/988,864

(22) Filed: Aug. 10, 2020

(65) Prior Publication Data
US 2021/0041519 A1    Feb. 11, 2021

(30) Foreign Application Priority Data
Aug. 8, 2019    (EP) .................................... 19190766

(51) Int. Cl.
*G01V 3/00*    (2006.01)
*G01R 33/561*    (2006.01)
(Continued)

(52) U.S. Cl.
CPC .......... *G01R 33/5619* (2013.01); *A61B 5/055* (2013.01); *A61B 5/7214* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

2007/0118399 A1* 5/2007 Avinash ................. G16H 10/60
                                                        705/2
2017/0052238 A1* 2/2017 Le Fur .................. G01R 33/465
(Continued)

FOREIGN PATENT DOCUMENTS

EP    2201525 A2 *    6/2010    ............... G06T 7/11
EP    2733672 A1 *    5/2014    ........... G06T 11/203

OTHER PUBLICATIONS

JP 2000513978 A (Year: 2000).*
(Continued)

*Primary Examiner* — Walter L Lindsay, Jr.
*Assistant Examiner* — Frederick Wenderoth
(74) *Attorney, Agent, or Firm* — Laurence A. Greenberg; Werner H. Stemer; Ralph E. Locher

(57) ABSTRACT

A method and a system automatically perform an image reconstruction of a biological object. The method includes acquiring at different time points t_i signal data for imaging the biological object and clustering a set of data in connection with the acquired signal data. The clustering includes constructing a matrix C, wherein an element $C_{i,j}$ of the matrix C is the value n_j of one of the data of the dataset acquired at the time point t_i, and then performing a similarity clustering based on the matrix C. At least one of the clusters is selected and determining for each of the time points t_i that are part of the cluster all acquired signal data that have been acquired within a predefined temporal threshold with respect to the considered time point t_i. The image reconstruction of the biological object is performed with the previously determined acquired signal data.

10 Claims, 5 Drawing Sheets

(51) Int. Cl.
    *A61B 5/055*     (2006.01)
    *A61B 5/00*     (2006.01)
    *G01R 33/56*     (2006.01)
    *G01R 33/565*     (2006.01)
    *G06T 11/00*     (2006.01)

(52) U.S. Cl.
    CPC .......... *A61B 5/742* (2013.01); *G01R 33/5608* (2013.01); *G01R 33/56509* (2013.01); *G06T 11/005* (2013.01); *G06T 11/008* (2013.01); *G06T 2207/10088* (2013.01); *G06T 2207/30048* (2013.01); *G06T 2210/41* (2013.01)

(58) Field of Classification Search
    USPC .......................................................... 324/309
    See application file for complete search history.

(56) References Cited

U.S. PATENT DOCUMENTS

| | | | |
|---|---|---|---|
| 2017/0091963 A1* | 3/2017 | Panin | A61B 6/037 |
| 2017/0199263 A1 | 7/2017 | Nickel | |
| 2017/0307707 A1 | 10/2017 | Huang et al. | |

OTHER PUBLICATIONS

Kim, Yong W. et al. "Coronary Magnetic Resonance Angiography for the Detection of Caronary Stenoses", Journal of Medicine, 2001, vol. 345, Nr. 26, pp. 1863-1869.

Van Heeswijk, Ruud B. et al. "Motion Compensation Strategies in Magnetic Resonance Imaging", Critical ReviewsTM in Biomedical Engineering, 2012, vol. 40, Nr. 2, pp. 99-119 inventon disclosure.

Koken, P. et al. "Advanced MR Sequences", ESMRMB Congress, 2015, Accelerated magnetic resonance fingerprinting, S97 inventon disclosure.

Bonanno, Gabriele et al. "Self-Navigation with Compressed Sensing for 2D Translational Motion Correction in Free-Breathing Coronary MRI: A Feasibility Study", CrossMark, PLOS One, 2014, doi:10.1371/journal.pone.0105523 inventon disclosure.

Pang, Jianing et al. "Whole-Heart Coronary MRA with 100% Respiratory Gating Efficiency: Self-Navigated Three-Dimensional Retrospective Image-Based Motion Correction (TRIM)", Magnetic Resonance in Medicine, 2014, vol. 74, pp. 67-74 inventon disclosure.

Piccini, Davide et al. "Four-Dimensional Respiratory Motion-Resolved Whole Heart Coronary MR Angiography", Magnetic Resonance in Medicine, 2017, vol. 77, pp. 1473-1484 inventon disclosure.

Stehning, C. et al. "Free-Breathing Whole-Heart Coronary MRA With 3D Radial SSFP and Self-Navigated Image Reconstruction", Magnetic Resonance in Medicine, 2005, vol. 54, pp. 476-480.

Heerfordt, John et al: "A Similarity-Based Data Clustering Approach for Fast Reconstruction of Untriggered and Ungated Whole-Heart MRA"; Proceedings of the 31st Annual Conference of the Society for Magnetic Resonance Angiography, SMRA; Nantes, France; Aug. 28-30, 2019; p. 40; XP055664589 / Aug. 29, 2019 European Search Report.

Feng, Li et al. "XD-GRASP: Golden-Angle Radial MRI with Reconstruction of Extra Motion-State Dimensions Using Compressed Sensing", Magnetic Resonance in Medicine, 2016, vol. 75, pp. 775-788 inventon disclosure.

Feng, Li et al. "5D Whole-Heart Sparse MRI", Magnetic Resonance in Medicine, 2018, vol. 79, pp. 826-838 inventon disclosure.

Piccini, Davide et al. "Respiratory Self-Navigation for Whole-Heart Bright-Blood Coronary MRI: Methods for Robust Isolation and Automatic Segmentation of the Blood Pool", Magnetic Resonance in Medicine, 2012, vol. 68, pp. 571-579 inventon disclosure.

Larson, Andrew C. et al. "Self-Gated Cardiac Cine MRI", Magnetic Resonance in Medicine, 2004, vol. 51, pp. 93-102 inventon disclosure.

Deng, Zixin et al: "A post-processing method based on interphase motion correction and averaging to improve image quality of 4D magnetic resonance imaging:a clinical feasibility study"; British Journal of Radiology; vol. 92; No. 1095; Jan. 3, 2019; GB; pp. 1-7; ISSN: 0007-1285; XP055664621 / Jan. 3, 2019 European Search Report.

* cited by examiner

METHOD AND SYSTEM FOR IMPROVING MAGNETIC RESONANCE IMAGES

CROSS-REFERENCE TO RELATED APPLICATION

This application claims the priority, under 35 U.S.C. § 119, of European patent application EP 19190766, filed Aug. 8, 2019; the prior application is herewith incorporated by reference in its entirety.

BACKGROUND OF THE INVENTION

Field of the Invention

The present disclosure is directed, in general, to imaging techniques for imaging biological objects, like tissues, and more specifically to techniques for imaging moving objects, like the heart, in the medical domain, in particular in the field of Magnetic Resonance Imaging (MRI).

When imaging moving organs, such as the heart or the liver, with a relatively slow acquisition technique such as MRI, motion and motion-related artifacts need to be addressed effectively. Occasionally, the motion problem is present also for structures that do not intrinsically move, such as the brain, when the patients cannot lay still in the MRI scanner for the whole duration of the acquisition. In general, "motion handling" techniques are either directed to trigger or gate the acquisition to a quiescent motion period (e.g. mid diastole or end-expiration), or to extract the motion information and use it e.g. for rejecting or correcting the motion-corrupted data. When it comes to extracting the motion information, it is very important to be able to either physically measure the displacement that needs to be corrected for, or to sort the acquired data into "motion-state-consistent" bins (bins where all the data correspond to a similar anatomical position/motion state) that can either be used to create sub-images that can then be registered to each other or employed in a motion-resolved reconstruction.

However, the identification of such motion consistent bins is usually based on techniques that make prior assumptions about the physiological processes that give raise to the motion signals. Such signals can be either extracted from the data itself or from external sources as the ECG or a respiratory belt (or e.g. a camera, when it comes to head motion). Similarly, contrast dynamics (e.g. after a gadolinium injection) need to be binned into "contrast-state-consistent" states (where all data has roughly the same contrast) in order to visualize the effect of these changes in the whole imaged anatomy.

Several methods have been implemented and tested that allow to extract physiological signals or contrast dynamics from different MRI acquisitions. As for the physiological signals, the most common techniques used are navigator gating (for the respiration) and ECG-gating (for the cardiac motion). These two make use of a signal source other than the imaging (i.e. the diaphragmatic navigator and the ECG) to extract the motion information. Contrast changes are either predicted by a priori knowledge of the injection mechanisms and contrast dynamics or extracted from images acquired at a high enough temporal resolution. A more recent, but very effective alternative, is the technique referred to as "self-navigation" or "self-gating". This technique is based on the extraction of the physiological and dynamic signals directly from the imaging data, by e.g. utilizing a portion of k-space (usually k-space center, a 1D readout or even a low-resolution 2D acquisition) that is consistently sampled at a high enough temporal frequency. The motion information extracted with these techniques can be influenced at the same time by physiological changes with different frequency contents, contrast dynamics, acquisition imperfections and other factors and needs therefore to be heavily filtered. For instance, to extract a respiratory/cardiac motion signal, the raw signal is usually first decomposed by using e.g. principal component analysis (PCA) or independent component analysis (ICA). Afterwards, the components need to be filtered or selected based on how their frequencies relate to prior assumptions about the underlying phenomena: e.g. around 0.3 Hz for respiration, 1-2 Hz for cardiac, and around the DC component for slow contrast dynamics.

BRIEF SUMMARY OF THE INVENTION

It is an objective of the present invention to propose a method and a system for improving medical images acquired for an object for which at least one part is subject to a physiological motion and/or a contrast change during image data acquisition.

The objective is achieved according to the present invention by a method and a system for automatically performing an image reconstruction according to the object of the independent claims. Dependent claims present further advantages of the invention.

Advantageously and in particular, the present invention allows one to create motion-state- and/or contrast-state-consistent data bins from acquired MRI data without explicit knowledge of—or a priori assumptions on—the motion signals and/or of contrast dynamics.

The present invention proposes a method for automatically performing an image reconstruction for a biological object. The method containing the following steps, each being carried out preferentially automatically:

a) acquiring signal data for imaging the biological object, for instance MRI signal data, wherein the signal data are acquired at different time points $t\_i$ and are configured for enabling an image reconstruction of the biological object;

b) clustering a set of data, wherein the set of data contains at least a part of the acquired signal data and/or data obtained from and/or together with the acquired signal data for each or a part of the different time points $t\_i$. In the case wherein the set of data contains data $d\_e$ obtained together, e.g. during a same measurement session, with the acquired signal data, e.g. data coming from an external device and acquired simultaneously with the signal data, then a same contrast change and/or physiological motion might appear slightly shifted with respect to the time point $t\_i$ at which the signal data have registered the contrast change and/or physiological motion and the time point $t\_k$ at which the data $d\_e$ also registered the contrast change and/or physiological motion. Nevertheless, the time points $t\_i$ and $t\_k$ are typically close, i.e. few milliseconds, to each other, and therefore, for simplification, all data acquired in a neighborhood (typically of few milliseconds) of $t\_i$ is considered to correspond to a similar or same motion- and/or contrast-state. Hence, if the measurements from an external device are slightly off, then the data $d\_e$ corresponding to the measurements are simply shifted with respect to the acquired signal data that are associated with at a given time point. The clustering contains:

bi) constructing a matrix C, wherein one dimension T of the matrix C corresponds to the time and equals a number of the different time points $t\_i$ associated to the data of the dataset, for instance the number representing a selection of some or all of the time points t_i, and wherein at least one other dimension N contains for each time point t_i of the dimension T at least a part of the data of the dataset acquired at the time point t_i, the dimensions N equaling therefore a number of data of the set of data acquired for at least one of the time points t_i, preferentially for every time point t_i, so that with respect to the dimensions T and N, an element $C_{i,j}$ of the matrix C (whose dimension is T×N) is the value n_j of one of the data of the dataset acquired at the time point t_i. In particular, the matrix C may comprise several dimensions N_j, j=1, . . . , k, wherein each dimension equals a number of data of the set of data acquired for at least one of the time points t_i, preferentially for every time point t_i, wherein the matrix C is filled with the values of the data of the dataset that have been acquired or obtained for each time point t_i, each row with respect to the dimension T containing therefore data of the dataset that have been obtained for the same time point t_i. For instance C is a 2D matrix T×N=256×512 containing elements $C_{i,j}$, wherein the element $C_{i,j}$ is equal to the value n_j of one of the data of the dataset acquired at the time t_i, wherein for each t_i, the dataset comprises preferentially 512 data, wherein i=1, . . . , 256 and j=1, . . . , 512;

bii) performing a similarity clustering based on the matrix C, e.g. directly on the matrix C or on a transformed version of the matrix C (e.g. a matrix C' obtained after dimensionality reduction of the matrix C), wherein time points t_i for which data values are close, i.e. whose difference is smaller than a threshold value (e.g. automatically calculated by the processing unit from a statistical distribution of at least some of the values n_j), are grouped together to form one or several clusters of data of the dataset. The similarity clustering according to the invention is performed free of any a priori information or assumption regarding a motion of at least one part of the biological object and/or of a contrast dynamic. The clustering of the different time points t_i is therefore based on similarities of their associated data with respect to the dataset;

c) selecting at least one of the clusters, e.g. a single one of the clusters or several of them, e.g. the largest one or the one with the highest degree of similarity between the data from the different time points t_i that have been grouped together to form the cluster, and determining (e.g. for each selected cluster, or for all selected clusters) for each of the time points t_i that are part of the selected cluster(s), i.e. that have been grouped together to form the cluster(s), all acquired signal data that have been acquired within a predefined temporal threshold with respect to the considered time point t_i;

d) performing image reconstruction of the biological object with the previously determined acquired signal data, and preferentially only said previously determined acquired signal data.

The present invention proposes also a system for automatically performing an image reconstruction of a biological object. The system contains:
a) optionally, an imaging system, like an MRI system, configured for acquiring signal data for imaging the biological object;
b) a memory for storing the acquired signal data;
c) a processor configured for processing the acquired signal data in order to reconstruct an image of the biological object;
d) optionally a display for displaying a reconstructed image of the biological object; and
e) characterized in that the processor is configured for automatically carrying out the previously described method.

The foregoing has broadly outlined the features and technical advantages of the present disclosure so that those skilled in the art may better understand the detailed description that follows. In particular, the present invention enables to extract the largest motion-state-consistent subset from the acquired signal data and therefore to reconstruct a static image out of a motion-corrupted acquisition, or to sort the acquired signal data into several motion-state-consistent bins and use them as an input for a motion-resolved reconstruction.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Other features which are considered as characteristic for the invention are set forth in the appended claims.

Although the invention is illustrated and described herein as embodied in a method and a system for improving magnetic resonance images, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

FIGS. 1 to 5, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Figure 1:
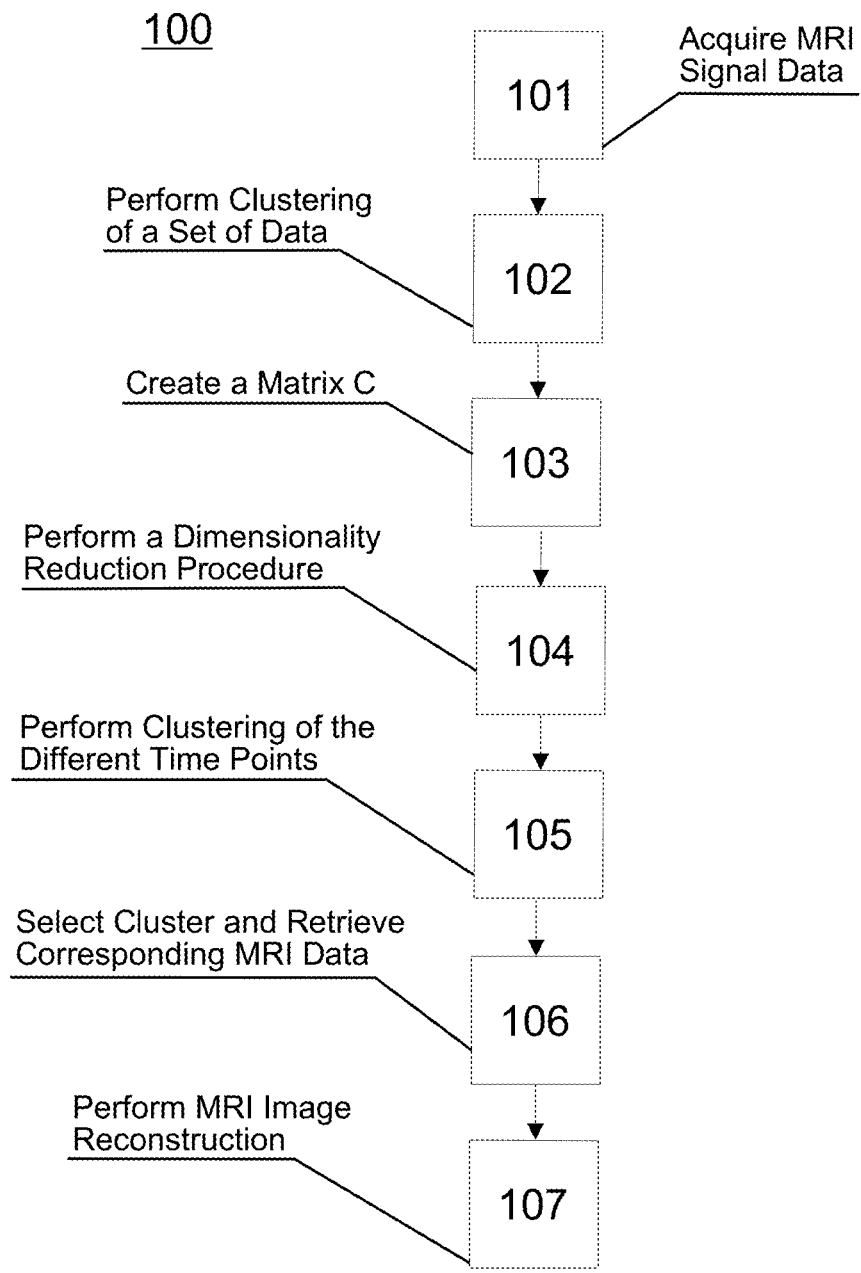
FIG. 1 is a flowchart showing a method for automatically performing an image reconstruction of a biological object according to the invention.

We will now describe in more details the method according to the invention through FIG. 1 which describes the different steps of a method 100 carried out by a system according to the invention for automatically performing an image reconstruction. In the following description, MRI technique will be taken for illustrating the present concept, but other medical imaging techniques might be used for performing an image reconstruction according to the present concept.

At step 101, the system according to the invention acquires MRI signal data of a biological object. Typically, the biological object may undergo some physiological motion and/or contrast changes, which need to be taken into consideration for reconstructing a sharp image of the biological object. Preferentially, one of the following techniques is used for acquiring the MRI signal data:
(a) a pulse sequence wherein at least one spatial frequency is sampled at different time points t_i during the acquisition, or
(b) a pulse sequence that allows for reconstruction of undersampled real-time images from signal data acquired at different time points t_i of the acquisition, or
(c) a standard pulse sequence in combination with an external device that is configured for measuring one or more signals that are modulated by motion of at least one part of the biological object at several time points t_i of the acquisition.

At step 102, the system according to the invention performs, preferably automatically, a clustering of a set of data which contains at least a part of the previously acquired MRI signal data and/or data obtained from or together with the acquired MRI signal data for each or a part of the different time points t_i. For instance, the set of data may comprise, with respect to the previously described techniques:
a) for technique (a): repeatedly sampled spatial frequencies or a transformed version thereof;
b) for technique (b): real-time images;
c) for technique (c): signals from the external device.

At step 103, the system automatically creates a matrix C based on the above-mentioned dataset. The matrix C contains one dimension T associated to the time and at least one dimension associated to the data of the dataset. In other words, the matrix C may comprise a certain number of rows, wherein each row corresponds to a different time point t_i and is filled with data values of the dataset that have been acquired at the time point t_i. For instance, the system is configured for selecting:
a) for technique (a), the repeatedly sampled spatial frequencies or the transformed version thereof,
b) for technique (b), the real-time images,
c) for technique (c) the signals from the external device, and the system automatically places the latter in the matrix C wherein one dimension corresponds to the different time points t_i and one or more dimensions contain the data that is available for every time point t_i with respect to the technique used for acquiring the data of the dataset. In particular, if several receiver coils are used to receive the MR signal, then the system according to the invention is configured for automatically performing a data augmentation (by concatenation or combination) when using technique (a), using the fact that the same spatial frequencies are received by all the coils.

At step 104, and optionally, if a large number of data is associated with each time point t_i, then the system is configured for performing a dimensionality reduction procedure in order to decrease the number of data available for each time point t_i.

At step 105, the system is configured for performing a clustering of the different time points, based on the similarity of their associated data as represented in the matrix C, in order to separate them into distinct clusters.

At step 106, the system is configured for automatically selecting one of the clusters and extracting all the MRI signal data that were performed in close adjacency to the time points t_i belonging to the selected cluster.

At step 107, the system is configured for automatically performing the MRI image reconstruction of the biological object using the MRI signal data that have been previously extracted at step 106 in connection with the selected cluster.

Figure 2:
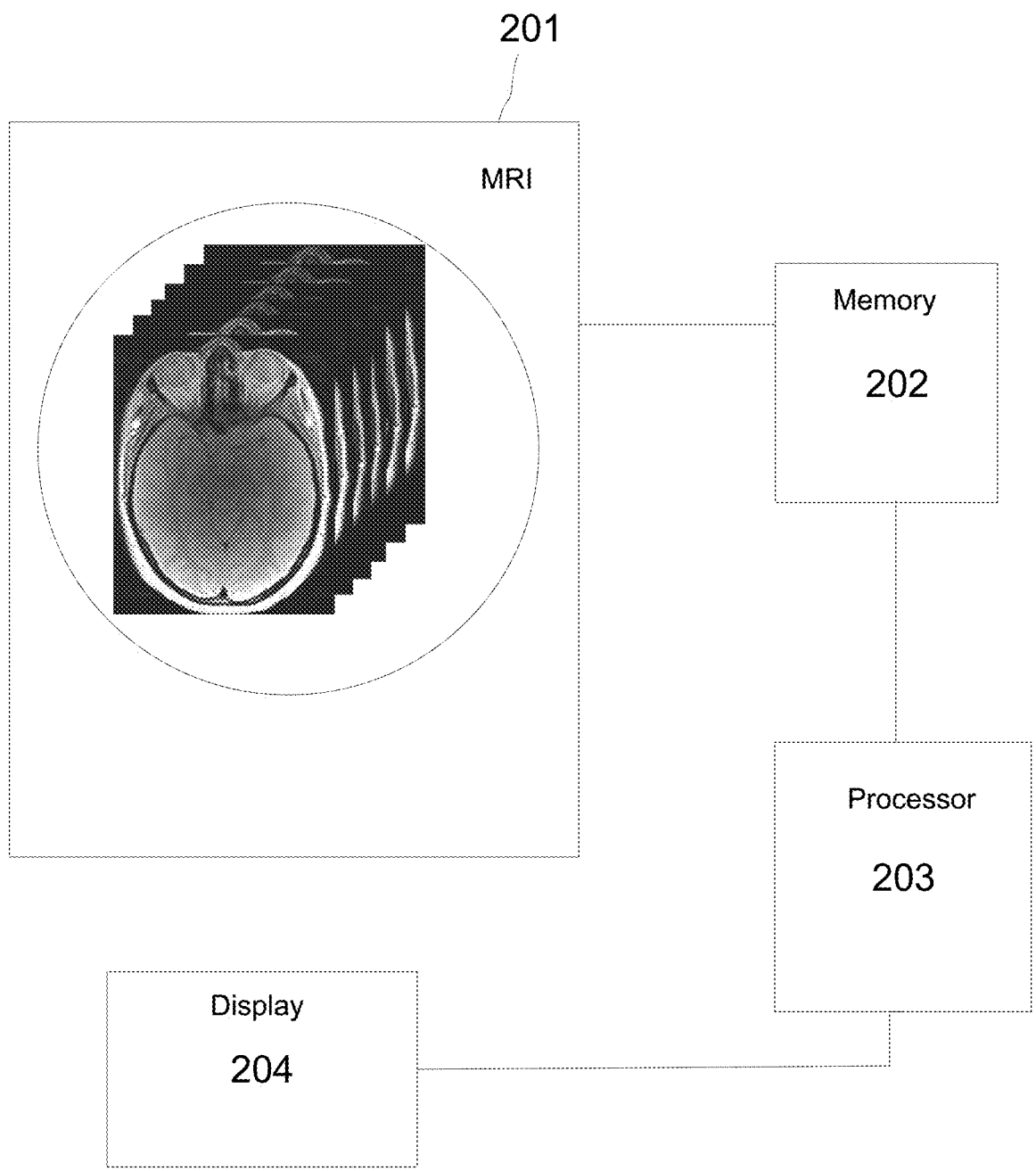
FIG. 2 is an illustration of a system for implementing the claimed method.

FIG. 2 illustrates a system 200 for automatically performing image reconstruction of a biological object. The system 200 contains:
a) optionally, a MRI imaging system 201, for acquiring MRI signal data which are typically used for the reconstruction of an image of a biological object. Variations of the MRI signal data are correlated to variations of one or several tissue characteristics at some spatial locations within the biological object;
b) a memory 202, connected to the MRI imaging system 201, for storing the acquired MRI signal data;
c) a processing unit 203 connected to the memory 202, typically a processor or controller, for processing the acquired signal data in order to reconstruct an image of the biological object, e.g. a 3D image of structures of the biological object;
d) optionally, a display 204 for displaying the reconstructed image provided by the processing unit 203; and
e) the system 200 being configured for carrying out the steps of the previously described method.

Compared to existing techniques, the present invention proposes to skip altogether the steps related to the physiological, dynamic, or generic motion signal extraction and proposes instead to intrinsically separate the acquired signal data into motion and contrast consistent bins obtained from the clustering of the matrix elements by leveraging the similarities among the elements, i.e. the acquired signal data (e.g. among the amplitude/phase of the center of k-space that is sampled along all the MRI measurements or among the 1D readouts that are acquired regularly as mentioned as described in Stehning et al., Magn Reson Med (54), 476 (2005)) without any prior knowledge about motion. According to the present invention, the similarity within the acquired signal data can be explored in any n-dimensional space with respect to the matrix C and with any sort of clustering technique that may be suitable for such a task. For instance, consistent 1D readouts acquired during an e.g. 5 min-long radial acquisition can be used as input for a Principal Component Analysis (PCA) algorithm that provides n (e.g. n=50) principal components, which form the data of the dataset obtained from the acquired data signal. These n components can be then considered as the dimensions of an n-dimensional space, i.e. the matrix C, where each of the consistent 1D readouts corresponds to one single data point residing in that space. A clustering algorithm is then applied to obtain a binning of the data as shown in FIGS. 3A-3C.

Figure 3C:
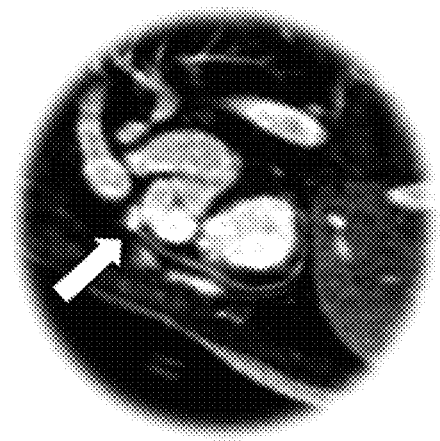
FIGS. 3A-3C are illustrations showing a first example of clustering according to the present invention.
Figure 3B:
Figure 3A:
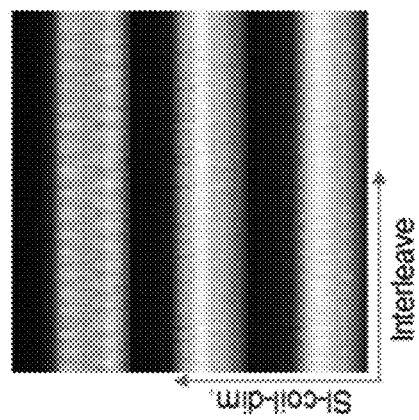
Figure 4A:
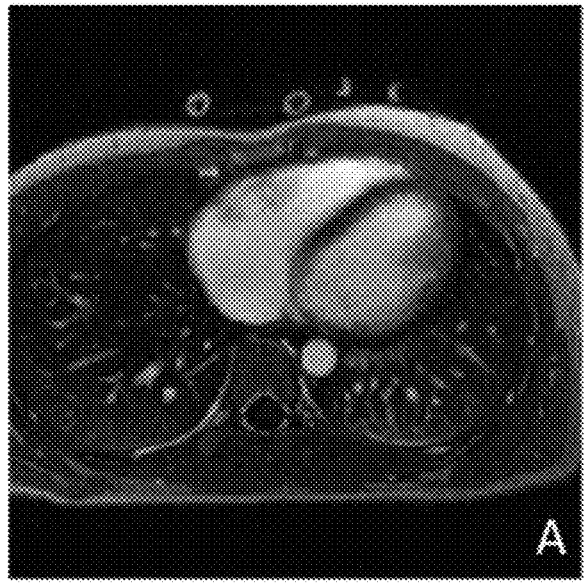
FIGS. 4A-4D are images of an example of comparison between an image reconstruction based on all acquired signal data (FIGS. 4A, 4C) and an image reconstruction based on selected bins according to the present invention.
Figure 4B:
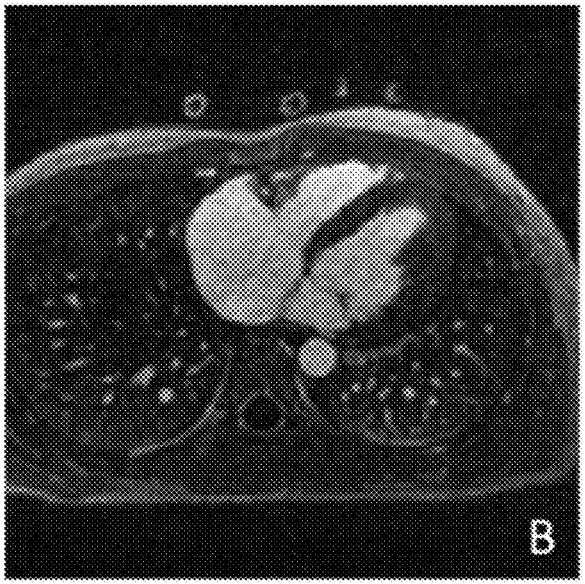
Figure 4C:
Figure 4D:

More precisely, FIGS. 3A-3C illustrate a clustering obtained when using such a clustering algorithm: in FIG. 3A, a matrix C is shown wherein all or some of the MRI signal data acquired from the coil elements for all coherently sampled readouts (e.g. superior-inferior (SI)) are stored within the matrix C and used as an input for the clustering algorithm. The time points t_i are related to the different interleaved acquisitions in function of the time. Optionally, a dimensionality reduction, using for instance PCA, is applied to the initial matrix C to create a n-dimensional space where each SI readout, or group of SI readouts from several coils but in the same time point t_i, is represented by a single point. FIG. 3B shows the resulting clustering, wherein the largest cluster (or, e.g., the most compact one) formed by these points and detected with a binning/clustering algorithm (e.g. k-means) is chosen to create a motion-consistent static image reconstruction free of any knowledge of the underlying physiology. FIG. 3C shows an example of the obtained reconstructed image. Because of the temporally uniform sampling (in this case a 3D radial kooshball trajectory implementing a golden angle rotation between interleaves), a coherent image can be reconstructed where sharpness of the features and general appearance are visibly improved when compared to a reconstruction where all acquired data are grouped together.

Figure 5:
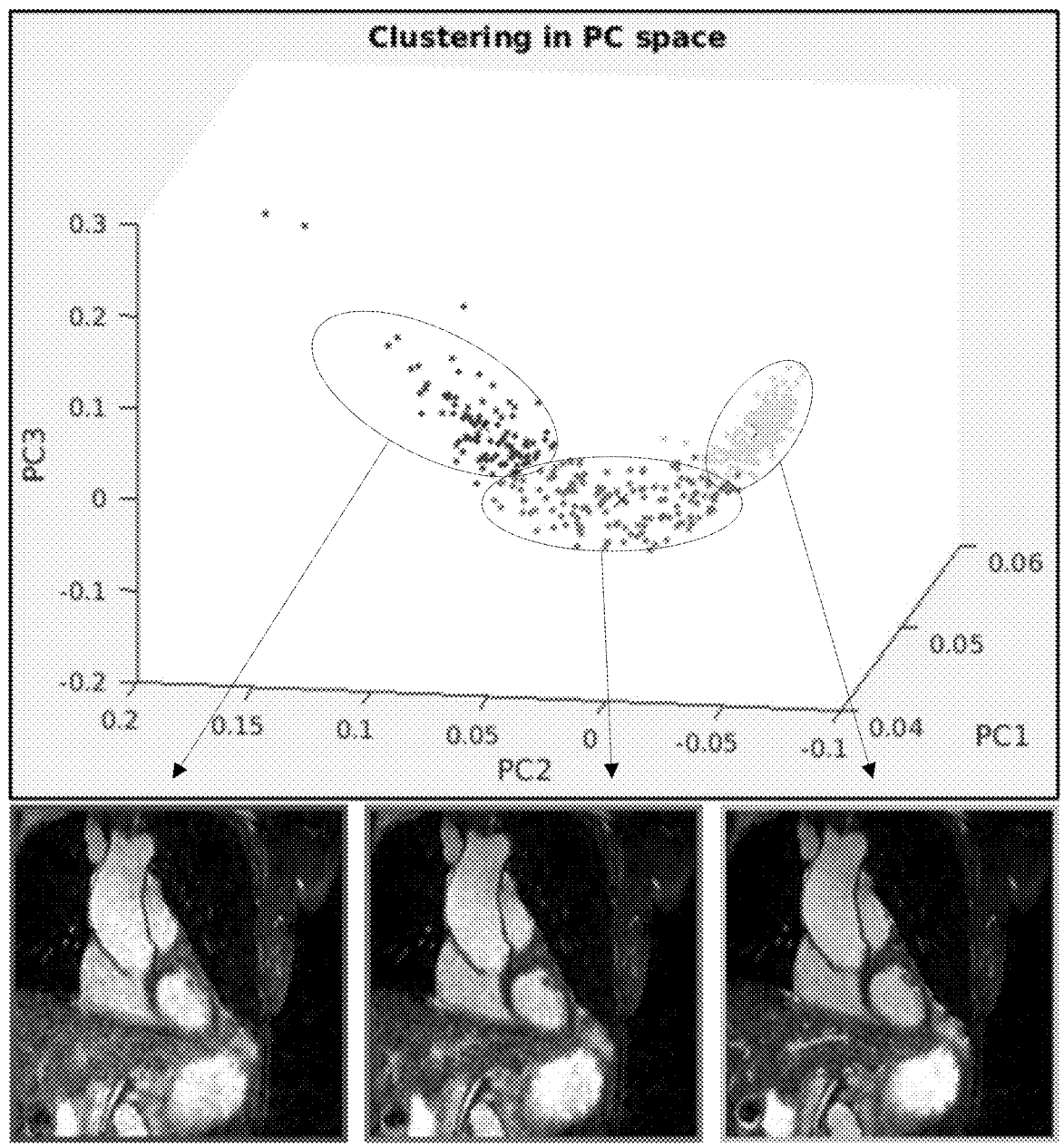
FIG. 5 is an illustration of a second example of clustering according to the present invention.

The described technique can be used, for instance, either to intrinsically extract the largest motion-state-consistent subset of acquired signal data and therefore reconstruct a static image out of a motion-corrupted acquisition as shown in FIGS. 4A-4D, or to sort the acquired signal data into several motion-state-consistent bins/clusters and use them as an input for a motion-resolved reconstruction as in described in Feng et al., Magn Reson Med (79), 826 (2018) and shown in FIG. 5 in order to perform the final image reconstruction. FIGS. 4A-4D present for instance a comparison between images obtained from a classic reconstruction based on all the acquired signal data (FIGS. 4A, 4C) and a reconstruction based on the present concept (FIGS. 4B, 4D), which clearly show a better result. In FIG. 5, the concept of the invention as described in FIGS. 3A-3C is further used for identifying more than one motion consistent bin (or cluster) and exploit their similarity using and XD-GRASP reconstruction.

Compared to existing techniques, the present invention has several advantages.

First of all, the claimed method is free of any assumption about physiology in the n-dimensional binning (and therefore avoid the step of explicitly extracting any kind of motion signal from the acquired signal data) allowing therefore to potentially work with arrhythmia, irregular breathing and any other kind of irregular motion (e.g. bulk motion).

Second, the same technique can be either readily applied to achieve a static reconstruction of a motion-state-consistent dataset, extracted from an untriggered/ungated acquisition and/or used as a pre-processing step of more complex reconstruction pipelines (e.g. when registration or motion-resolved reconstruction is needed).

Third, avoiding the step of explicit motion extraction potentially allows for a considerable decrease in reconstruction times.

To summarize, the claimed technique does not rely on a specific signal extraction, but solely on similarities within the acquired signal data, wherein a binning/clustering of the acquired signal data takes place in a n-dimensional space with respect to the different time points t_i of acquisition and that is not necessarily directly related to the acquisition space (e.g. k-space) nor the image space. The described technique provides a very easy solution for obtaining a static image of a moving organ (e.g. the heart) without any complexity on the planning/protocol/sequence side, but just using a continuous acquisition. For instance, the present invention might be applied to coronary MR imaging without any triggering nor gating with almost instantaneous reconstruction at the scanner.

The invention claimed is:

1. A method for automatically performing an image reconstruction of a biological object, which comprises the steps of:

acquiring, for different time points t_i, magnetic resonance imaging (MRI) signal data for imaging the biological object, the MRI signal data being acquired using a MRI imaging system and stored in a memory;

clustering a set of data using a processor receiving the MRI signal data, wherein the set of data containing at least a part of the MRI signal data acquired and/or data obtained from and/or together with the MRI signal data acquired for each or a part of the different time points t_i, wherein the clustering further comprises:

constructing a matrix C, wherein one dimension T of the matrix C equals a number of the different time points t_i associated to data of a dataset, and wherein at least one other dimension N equals a number of the data of the set of data acquired for every time point t_i, so that with respect to the dimensions T and N, an element $C_{i,j}$ of the matrix C is a value n_j of one of the data of the dataset acquired at a time point t_i;

performing a similarity clustering of the different time points t_i based on the matrix C, wherein a time point t_i for which the data values are close to data values of another time point is grouped with the another time point in order to form clusters, wherein data values of the time point t_i are considered close to the data values of the another time point if their difference is smaller than a threshold value;

selecting at least one of the clusters and determining for each of the different time points t_i that are part of the at least one cluster all acquired signal data that have been acquired within a predefined temporal threshold with respect to a considered time point t_i from the different time points t_i;

performing the image reconstruction of the biological object with previously determined acquired signal data; and displaying a reconstructed image provided by the processor on a display.

2. A system for automatically performing image reconstruction of a biological object, the system comprising:

a memory for storing acquired magnetic resonance imaging (MRI) signal data acquired at different time points t_i;

a MRI imaging machine having coil elements for acquiring the acquired MRI signal data;

a processor configured for processing the acquired MRI signal data in order to reconstruct an image of the biological object, wherein said processor is configured to:

cluster a set of data, wherein the set of data containing at least a part of the acquired MRI signal data and/or data obtained from and/or together with the acquired MRI signal data for each or a part of the different time points t_i, wherein the clustering further comprises:

constructing a matrix C, wherein one dimension T of the matrix C equals a number of the different time points t_i associated to data of a dataset, and wherein at least one other dimension N equals a number of the data of the set of data acquired for every time point t_i, so that with respect to the dimensions T and N, an element $C_{i,j}$ of the matrix C is a value n_j of one of the data of the dataset acquired at a time point t_i;

performing a similarity clustering the different time points t_i based on the matrix C, wherein a time point t_i for which the data values are close to data values of another time point is grouped with the another time point in order to form clusters, wherein data values of the time point t_i are considered close to the data values of the another time point if their difference is smaller than a threshold value;

select at least one of the clusters and determining for each of the different time points t_i that are part of the at least one cluster all acquired signal data that have been acquired within a predefined temporal threshold with respect to a considered time point t_i from the different time points t_i; and perform the image reconstruction of the biological object with previously determined acquired signal data; and a display for displaying a reconstructed image provided by said processor.

3. The method according to claim 1, wherein the matrix C contains several dimensions $N\_j, j=1, \ldots, k$, wherein each dimension equals a number of the data of the set of data acquired for one of the different time points t_i.

4. The method according to claim 1, wherein the similarity clustering is performed free of any a priori information or assumption regarding a motion of at least one part of the biological object and/or of a contrast dynamic measured for the biological object.

5. The method according to claim 1, wherein a largest cluster or a cluster with a highest degree of similarity is selected.

6. The method according to claim 1, wherein one of the following techniques is used for acquiring the signal data:
  a) a pulse sequence wherein at least one spatial frequency is sampled at the different time points t_i during an acquisition; or
  b) a pulse sequence that allows for reconstruction of undersampled real-time images from the signal data acquired at the different time points t_i of the acquisition; or
  c) a standard pulse sequence in combination with an external device that is configured for measuring at least one signal that is modulated by motion of at least one part of the biological object at several time points t_i of the acquisition.

7. The method according to claim 6, wherein the set of data comprises:
  for technique (a): repeatedly sampled spatial frequencies or a transformed version thereof;
  for technique (b): real-time images; and
  for technique (c): signals from the external device.

8. The method according to claim 6, wherein a system is configured for automatically performing a data augmentation when using the technique (a) if several receiver coils are used for magnetic resonance signal reception.

9. The method according to claim 1, which further comprises performing a dimensionality reduction procedure in order to decrease a number of the data available for each of the different time points t_i.

10. The method according to claim 1, wherein the matrix C contains all or some of magnetic resonance imaging (MRI) signal data acquired from coil elements of a MRI system for all coherently sampled readouts and wherein the different time points t_i are related to different interleaved acquisitions in function of time.

* * * * *